United States Patent
Miraki

(10) Patent No.: US 9,801,719 B2
(45) Date of Patent: Oct. 31, 2017

(54) ANNULUS RINGS WITH SUTURE CLIPS

(71) Applicant: Edwards Lifesciences Corporation, Irvine, CA (US)

(72) Inventor: Manouchehr A. Miraki, Laguna Hills, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 24 days.

(21) Appl. No.: 14/826,054

(22) Filed: Aug. 13, 2015

(65) Prior Publication Data
US 2016/0045313 A1    Feb. 18, 2016

Related U.S. Application Data

(60) Provisional application No. 62/037,918, filed on Aug. 15, 2014.

(51) Int. Cl.
*A61F 2/24* (2006.01)
*A61B 17/04* (2006.01)

(52) U.S. Cl.
CPC ........ *A61F 2/2448* (2013.01); *A61B 17/0487* (2013.01); *A61F 2/2445* (2013.01)

(58) Field of Classification Search
CPC ......... A61F 2/2445; A61F 2/2448; A61F 2/24
USPC .............................................. 623/2.36–2.37
See application file for complete search history.

(56) References Cited

U.S. PATENT DOCUMENTS

| | | | |
|---|---|---|---|
| 5,776,188 A | 7/1998 | Shepherd et al. | |
| 6,066,160 A * | 5/2000 | Colvin | A61B 17/0487 606/151 |
| 2009/0210051 A1 | 8/2009 | Camedda et al. | |
| 2009/0222083 A1 * | 9/2009 | Nguyen | A61B 17/00234 623/2.11 |
| 2011/0118832 A1 * | 5/2011 | Punjabi | A61F 2/2445 623/2.36 |
| 2011/0224714 A1 | 9/2011 | Gertner | |
| 2014/0013602 A1 * | 1/2014 | Wright | A61F 2/2448 29/896.9 |
| 2014/0031864 A1 * | 1/2014 | Jafari | A61B 17/0401 606/232 |

(Continued)

OTHER PUBLICATIONS

Int'l. Search Report for PCT/US2015/045374, Mailed Nov. 16, 2015.

*Primary Examiner* — Suzette J Gherbi
(74) *Attorney, Agent, or Firm* — Klarquist Sparkman, LLP

(57) ABSTRACT

Disclosed herein are annular prosthetic devices, such as annuloplasty rings, that include suture clips integrated into or mounted within an annular frame. The clips can quickly secure to sutures to obviate the need to tied knots in the sutures during implantation. Embodiments comprise an annular frame having an open central region and a plurality of suture clips spaced angularly apart around the frame. Each of the suture clips can comprise two opposing tabs that extend toward each other such that the suture clip forms a gripping region between ends of the tabs and the gripping region is configured to grip a suture inserted through the suture clip between the two tabs. The annular frame and the plurality of suture clips can be formed from a single piece of flat material with the suture clip tabs being formed by laser cutting the piece of flat material, or the suture clips can be movable along a track formed in the annular frame.

16 Claims, 3 Drawing Sheets

(56) References Cited

U.S. PATENT DOCUMENTS

| | | | |
|---|---|---|---|
| 2015/0018879 A1* | 1/2015 | Moehle | A61B 17/0487 606/232 |
| 2015/0230920 A1* | 8/2015 | Alfieri | A61F 2/246 623/2.36 |
| 2015/0257884 A1* | 9/2015 | Subramanian | A61F 2/2445 623/2.36 |
| 2015/0327994 A1* | 11/2015 | Morriss | A61F 2/2418 623/2.17 |
| 2015/0366556 A1* | 12/2015 | Khairkhahan | A61B 17/0401 606/232 |
| 2016/0015518 A1* | 1/2016 | Conklin | A61F 2/2496 623/2.37 |
| 2016/0166730 A1* | 6/2016 | Matheny | A61L 27/3633 623/2.36 |
| 2016/0213371 A1* | 7/2016 | Miraki | A61B 1/05 |
| 2016/0256278 A1* | 9/2016 | Conklin | A61F 2/2496 |
| 2016/0270776 A1* | 9/2016 | Miraki | A61B 17/0487 |

* cited by examiner

ANNULUS RINGS WITH SUTURE CLIPS

CROSS-REFERENCE TO RELATED APPLICATIONS

This application claims the benefit of U.S. Provisional Patent Application No. 62/037,918 filed Aug. 15, 2014, which is incorporated by reference herein in its entirety.

FIELD

The field of this disclosure is suture attachment devices and methods for placement of a prosthetic device at a native heart valve annulus.

BACKGROUND

Prosthetic devices are often implanted using sutures. For example, prosthetic heart valves and annuloplasty rings can be secured to a native heart valve annulus using sutures. Conventionally, the loose ends of the sutures are tied in knots to secure them together and/or to secure the prosthetic device to the adjacent tissue. However, the process of tying knots in sutures can be time consuming and difficult, the amount of slack left in the sutures can be difficult to control, the knots can be difficult or impossible to untie, and/or the knots can accidentally come loose. Thus, there is a need in the art for ways to secure prosthetic devices using sutures but without tying knots in the sutures.

SUMMARY

Disclosed herein are annular prosthetic devices, such as annuloplasty rings, that include suture clips integrated into or mounted within an annular frame. The clips can quickly secure to sutures to obviate the need to tied knots in the sutures during implantation.

Some embodiments comprise an annular frame having an open central region and a plurality of suture clips integrated with the frame and spaced angularly apart around the frame. Each of the suture clips can comprise two substantially equal sized opposing tabs that extend toward each other such that the suture clip forms a gripping region between ends of the tabs and the gripping region is configured to grip a suture inserted through the suture clip between the two tabs. The suture clips are configured to engage sutures inserted through the gripping region to restrict the inserted sutures from moving through the suture clips in a direction opposite of insertion. The annular frame and the plurality of suture clips can be formed from a single piece of flat material with the suture clip tabs being formed by laser cutting the piece of flat material.

The annular frame can comprises a generally D-shape configured for placement at a native mitral valve annulus, or can have other shapes configured form placement at other heart valve sites.

In some embodiments, the annular frame is configured to be attached to a prosthetic heart valve such that the suture clips are operable to anchor the prosthetic heart valve to the native mitral valve annulus via a plurality of sutures engaged within the suture clips.

Some exemplary annular devices comprise an annular frame comprising an inner frame portion having a first cavity that faces radially outwardly, and an outer frame portion positioned radially around the inner frame portion and having a second cavity that faces radially inwardly toward the first opening. The first and second cavities form an annular track around the annular frame between the inner frame portion and the outer frame portion. The device includes a plurality of suture clips positioned within the annular track, wherein one or more of the plurality of suture clips can move along the annular track relative to the annular frame. In some embodiments, one or more of the plurality of suture clips can also rotate or spin within the annular track relative to the frame.

An exemplary method for delivering a prosthetic annular device to a native heart valve annulus region comprises advancing the annular prosthetic device over an array of sutures, such that the sutures pass through a plurality of suture clips integrated into the annular prosthetic device. Each suture clip comprises a pair of opposing, resiliently flexible tabs that are configured to allow at least one suture to advance in one longitudinal direction through the suture clip while gripping the suture to prevent the suture from moving in an opposite longitudinal direction through the suture clip. The method can further comprise tightening the sutures relative to the annular prosthetic device by pulling the suture through the suture clips to anchor the annular prosthetic device adjacent to the native heart valve annulus region with the sutures at a desired tension.

In some embodiments, the method can further comprise adjusting the orientation of one or more of the plurality of clips relative to an annular frame of the annular prosthetic device. Adjusting the orientation of the clips can comprise sliding one or more of the clips along a track formed between an inner annular frame portion and an outer annular frame portion.

In some embodiments, the annular device can be delivery while mounted on a delivery handle. The method can further include activating a delivery handle connected to the annular prosthetic device to release the annular prosthetic device from the delivery handle once the sutures are positioned through the suture clips of the annular prosthetic device. Releasing the annular prosthetic device from the delivery handle can comprises removing portions of the delivery handle from within the suture clips to allow the suture clips to close onto the sutures passing through the suture clips.

The foregoing and other objects, features, and advantages will become more apparent from the following detailed description, which proceeds with reference to the accompanying figures.

DETAILED DESCRIPTION

Figure 1:
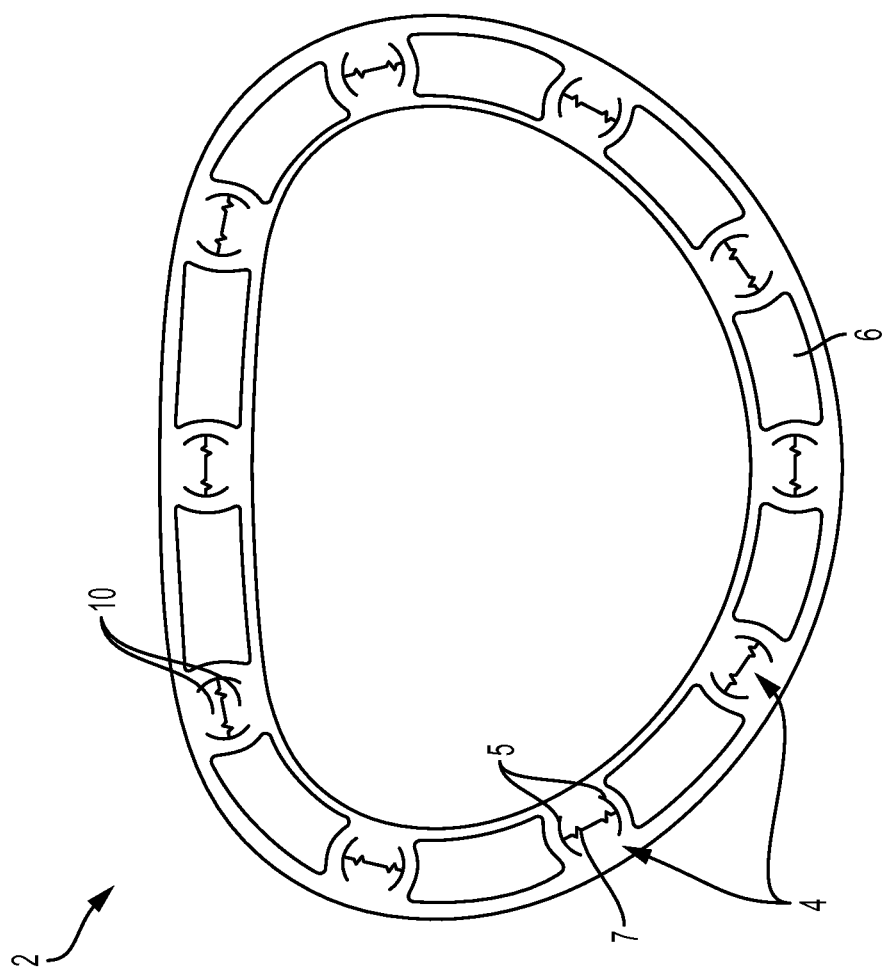
FIG. 1 is a plan view of an exemplary prosthetic ring with suture clips for implantation at the mitral valve annulus.

Rather than tying knots to secure sutures around a prosthetic device, the prosthetic device can include one or more suture securement devices, or suture clips, that are integrated into or mounted on the prosthetic device and can be used to engage sutures that retain the prosthetic device at a desired location relative to adjacent tissue.

The disclosed technology can be applied to prosthetic devices having annular or non-annular configurations, though the examples provided herein are primarily related to annular prosthetic devices, such as annuloplasty rings and anchors for prosthetic heart valves. "Annular," as used herein, refers to any shape substantially forming a ring, including non-circular shapes, such as the generally D-shaped device shown in FIG. 1, and including broken or interrupted ring shapes that are not fully annular and include a break or slot or gap. For prosthetic devices adapted for implantation at a native heart valve annulus, the precise shape of the device can be selected and/or adjusted to correspond the shape or desired shape of the target heart valve annulus and/or other specific heart geometry. For example, a D-shaped device may be especially useful for the mitral valve annulus.

In some embodiments, the prosthetic devices disclosed herein can be independent annular structures having an open central area. In other embodiments, the annular devices can be configured to be an anchoring device coupled to another device component, such as a prosthetic heart valve (i.e., a prosthetic mitral valve, prosthetic aortic valve, prosthetic tricuspid valve, or prosthetic pulmonic valve) and/or prosthetic heart devices. In such embodiments, a leaflet valve structure of the prosthetic heart valve can occupy and/or overlap the open, central portion of the annular anchoring device. In some embodiments, the annular anchoring device and a corresponding prosthetic heart valve can be manufactured to form a single device, whereas in other embodiments, they can be manufactured separately, and can be assembled by the surgeon or other user.

Use of the disclosed devices can confer one or more of the following exemplary advantages. In some examples, by using the disclosed devices rather than tying knots in the sutures, the sutures can be secured in less time and with less difficulty (especially in hard-to-reach locations). The suture clips can also be less likely to come loose from sutures compared to knots tied in the suture. In addition, some disclosed devices can allow the amount of slack left in the sutures after implantation to be more precisely controlled. Further, in embodiments where the suture clips share a common annular support frame, the suture clips can be physically restricted from traveling outside of the frame and away from the native valve annulus or other implantation site if the suture clips come loose from the engaged sutures. Furthermore, the disclosed prosthetic devices (and any attached devices) can be applied to the native valve annulus more quickly, lowering the cost in terms of personnel and facilities usage. Some disclosed devices can also be manufactured easily and at lower cost, yet can be robust functionally. The devices can also have a low-profile due to the flatness of the frame and clips, and may be foldable depending upon the materials chosen.

Each operative suture clip that is included in the disclosed prosthetic devices can secure a single suture, or two or more sutures at the same time. For ease of description, this disclosure may at times describe use with only a single suture, though it should be understood that the disclosed embodiments may be used with two or more sutures in the same or similar manner, unless otherwise described. Likewise, it should be understood that any of the disclosed embodiments describing use with two or more sutures can also be used with a single suture in the same or similar manner, unless otherwise described.

Each suture clip can be positioned on a suture by threading a free end of the suture through an opening in the suture clip and/or by sliding the suture laterally through a slit in the side of the suture clip, depending on the particular clip embodiment. Once a suture clip unit is engaged around a suture, the clip can prevent the suture from sliding axially through the unit in one or both longitudinal directions of the suture. In some embodiments, the suture clip can be biased to allow the sutures to readily slide through the clip in one longitudinal direction (such to tighten the suture), but prevent the sutures from sliding in the opposite longitudinal direction, forming a one-way suture lock, or ratchet mechanism. In other embodiments, the clip can prevent the suture from sliding in both longitudinal directions of the suture, forming a more restrictive two-way suture lock.

Exemplary embodiments of disclosed prosthetic devices are disclosed below and shown in the attached figures. These embodiments should not be construed as limiting in any way. Instead, the present disclosure is directed toward all novel and nonobvious features and aspects of the various disclosed embodiments, alone and in various combinations and sub-combinations with one another.

Exemplary Embodiments

FIG. 1 shows an exemplary annular prosthetic device in the form of an annuloplasty ring 2 that can be secured to a native mitral valve annulus using a plurality of suture clips 4 positioned around the ring. Each clip 4 can be secured to one or more sutures or suture segments (such as two ends of the same suture), instead of having to tie a standard suture knot. The sutures can extend from the annulus tissue and pass through the clips 4, allowing the ring 2 to be secured against or adjacent to the annulus tissue.

Figure 4B:
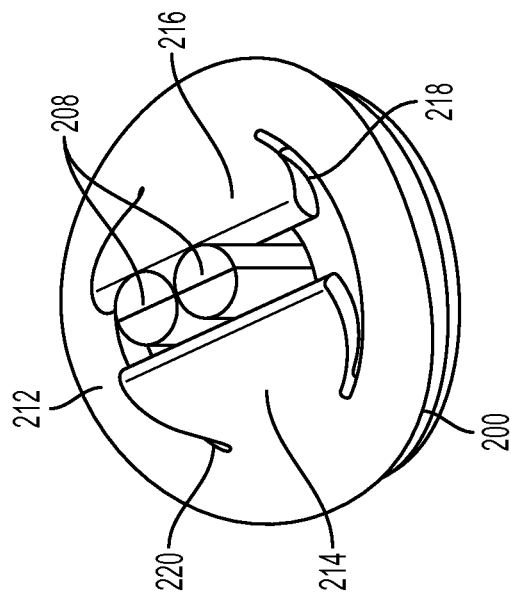
FIG. 4B is a perspective view of the clip of FIG. 4A, showing two suture segments extending through the clip.

Each clip 4 can comprise two tabs 10 between which the suture segments are inserted and secured (such as similar to as shown in FIG. 4B). The presence of sutures between the tabs 10 causes the tabs to be resiliently deflected apart, imparting a clamping force on the sutures. In this way, the clips 4 can prevent the engaged sutures from sliding through the clips 4 toward the native valve annulus, keeping the sutures taught and keeping the ring 2 secured against the mitral valve tissue 4. In some embodiments, the clips 4 allow the sutures to be further tightened after an initial deployment to reduce excess slack in the sutures. For example, in some embodiments, the sutures can be cinched after deployment by using a forceps.

Figure 4C:
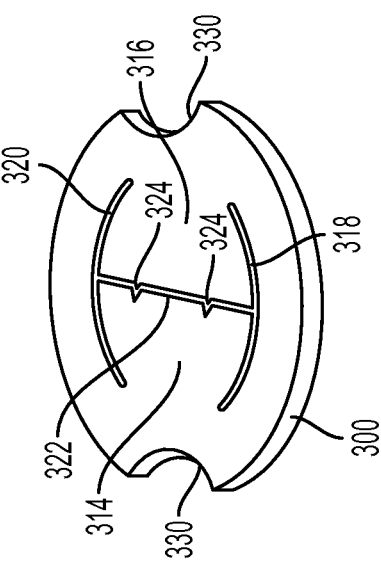
FIG. 4C is a perspective view of another exemplary suture clip, that is suitable for use in the ring of FIG. 2.
Figure 4A:
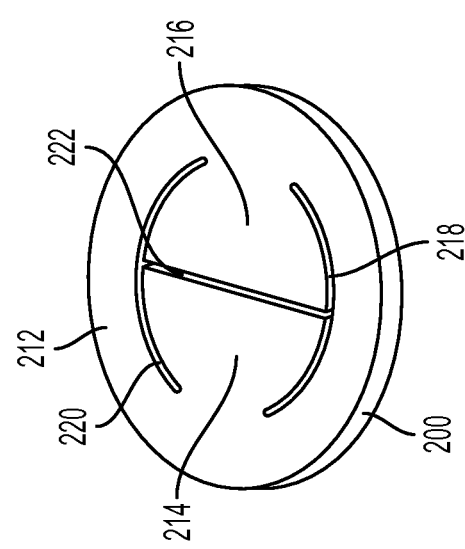
FIG. 4A is a perspective view of an exemplary suture clip that is suitable for use in the ring of FIG. 2.

The clips 4 are integrated into the structure of the ring 2, and can formed of the same material as the rest of the ring. The clips 4 can be formed by making cuts into a generally flat ring during manufacture, such as be using laser cutting techniques. The ring 2 can be substantially flat in a natural state prior to implantation. For each clip 4, the pattern of cuts can comprise two opposing arcuate cuts 5, and a single connecting cut 7 extending between the two arcuate cuts (a similar cut pattern is shown in FIG. 4A), thereby creating two generally semilunar tabs 10. The connecting cut 7 can be substantially straight (as shown in FIG. 4A), or can have an at least partially jagged or non-linear course (as shown in FIGS. 1 and 4C). In some embodiments, the clips 4 can include substantially straight cuts in place of the arcuate cuts 5, in which case, the tabs 10 can be substantial rectangular-shaped rather than semilunar.

The clips 4 can be spaced angularly apart around the ring 2 at roughly equal distances apart, as shown in FIG. 1.

However, in other embodiments, the clips 4 can also be spaced apart at non-equal distances, or in any desired spacing pattern. Ten clips 4 are included in the illustrated ring 2, although different numbers of clips can be used in other implementations. The number of clips 4 can be selected based on the size of the ring, for example, with a greater number of clips 4 included in embodiments having larger size/circumference. In some embodiments, the clips 4 can be distributed around the ring 2 in such a manner as to permit greater flexibility at certain locations along the ring 2. For example, in certain embodiments, fewer clips 4 may be present along portions of the ring 2 facing an atrial or ventricular septum to achieve higher levels of flexibility in these areas.

The ring 2 can further comprise one or more open areas or apertures 6 located between adjacent clips 4. The open areas 6 can be used, for example, for passing additional sutures through the ring to secure the ring 2 to the native tissue or other devices. The open areas 6 can also be configured to allow native annulus tissue to protrude therethrough (such as to promote tissue ingrowth), and can have rounded/atraumatic edges to permit a non-injurious interaction with the native tissue.

The ring 2 (including the clips 4) can be laser-cut, and can have a one-piece design. The ring 2 can then be polished and cleaned after the laser cutting. The ring 2 can be at least partially coated with a protective and/or soft material, such as silicone or another polymeric material. In some embodiments, the clips 4 are not covered by such a coating, while the remainder of the ring can be at least partially covered by the coating. In an exemplary method, the clip 4 areas can be masked (along their front and back surfaces) during the coating process. In some embodiments, the coating (not shown) can have a thickness of from about 0.005 inch to about 0.025 inch on each side (i.e., the top major surface and the bottom major surface) of the ring 2. The ring 2 itself (not including the coating) can have a suitable thickness to provide sufficient rigidity and flexibility for secure implantation at a native valve annulus, such as from about 0.010 inch to about 0.020 inch, with one example having a thickness of about 0.014 inch. Other embodiments can have thicknesses outside of these exemplary ranges.

The ring 2 can be made from any of various biocompatible materials, such as stainless steel, titanium, polymeric material, and/or nitinol. In some embodiments, one or more of the clips 4 can be made from a different material than the rest of the ring 2. For example, in some embodiments, the clips 4 are made from titanium or stainless steel, while the rest of the ring 2 is made from Nitinol. In various embodiments, the ring 2 can be resiliently deformable and/or malleable, such that the shape of the ring 2 can be temporarily or permanently adjusted by the surgeon during implantation to better fit the native annulus of a particular patient, or such that the ring 2 can be configured to flex (after implantation) to move in concert with the annulus during cardiac cycling.

The ring 2 can be relatively thinner at least in the areas of the clips 4 (e.g., from about 0.005 inch to about 0.015 inch thick) and/or can be thicker in areas between the clips. In other embodiments, the ring 2 can have a uniform thickness (e.g., from about 0.010 inch to about 0.020 inch thick). In particular embodiments, ring 2 has sufficient rigidity and/or resilience to reshape the valve annulus when secured implanted. In other embodiments, the ring 2 can be a relatively thin ring mounted to a more rigid base ring, which ring base can have apertures aligned with the clips 4 through which the sutures can pass.

The integrated-clip design of the ring 2 can alternatively be incorporated into any type of prosthetic heart valve device, other types of ring devices, or pledget devices. The ring 2 can be configured to accommodate any type of suture diameter or suture material.

In some embodiments, the ring 2 can be collapsible and/or radially compressible, such that the ring 2 can be delivered via a transcatheter method, either alone or along with a prosthetic heart valve or other prosthetic device. In some cases, the ring 2 can be coupled to a transcatheter heart valve, in a collapsed state, and delivered to the native valve annulus, where the ring 2 and prosthetic valve can be subsequently expanded to their functional configurations. In various embodiments, the ring 2 can be delivered via a transatrial, transventricular, or transeptal approach. The ring 2 can be secured to the annulus by itself (via sutures), or can be coupled to at least one other prosthetic device when secured to the annulus. Such other prosthetic devices can include, for example, prosthetic heart valves, stents, grafts, and various other prosthetic implants conventionally secured to tissue using sutures.

The ring 2 can be temporarily connected to a handle (not shown) for surgical implantation. The handle can hold the ring 2 fixed in position, and can also keep the clips 4 open during suture placement between the tabs 10. In some embodiments, the handle can have flat or rounded finger elements that can push the tabs 10 open and keep them open during suture placement. Within the handle, there can be slits disposed in a circular arrangement that allow the user to place the suture segments 8, such that they can be cinched or otherwise tensed prior to releasing the ring 2. The handle can further comprise a ring push-out feature that releases the ring 2 at a desired implantation site at the native valve annulus.

To deliver the ring 2 to the native valve annulus using a handle, the ring 2 can be loaded over the handle with the sutures already placed into the native valve annulus and extending therefrom. The suture segments can be configured to extend from the native annulus (towards the ring). With the ring 2 held in position using the handle (such as by an assistant), the surgeon or other user can feed the free ends of suture segments through the openings of the clips 4. Once all suture segments are inserted within their respective clips, the user can parachute the ring 2 downwards (towards the native valve annulus) to its desired position over the native valve annulus. The surgeon can then place tension on each of the suture segments and cinch them relative to the ring. The ring can then be released from the handle with the suture segments locked in position within the clips 4. The handle can be removed from the native valve annulus region and the suture segments cut, such as with a surgical blade. Further description regarding exemplary handles and systems for implanting a ring device, such as ring 2, are provided in U.S. Patent Application Publication No. 2013/0331930, published Dec. 12, 2013, which is incorporated by reference herein in its entirety.

Figure 2:
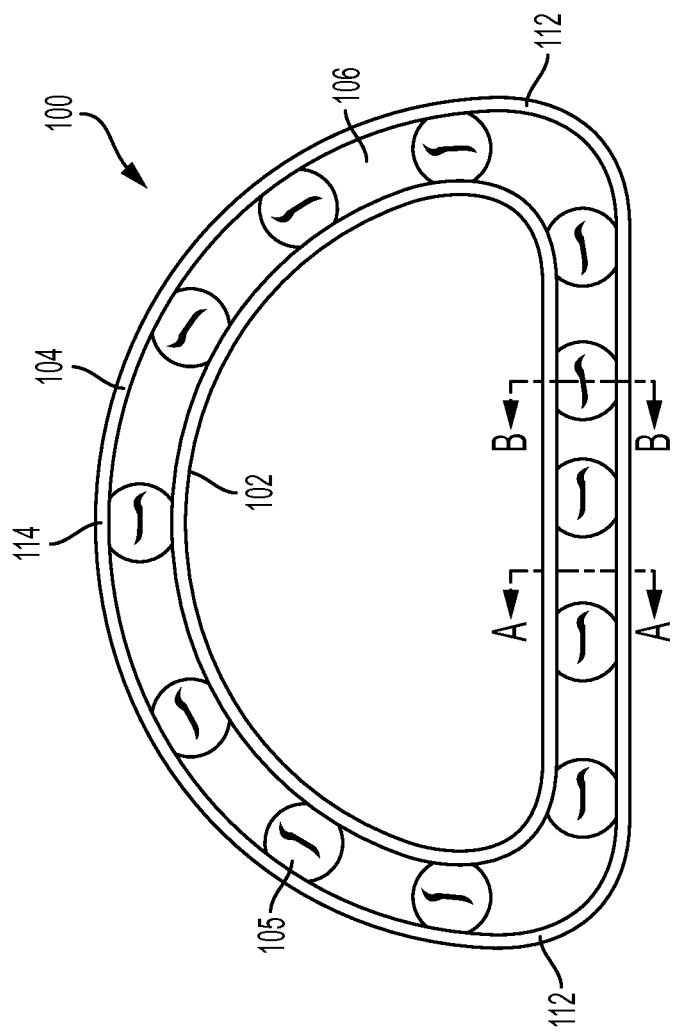
FIG. 2 is a plan view of another exemplary prosthetic ring for implantation at the mitral valve annulus, having movable suture clips.
Figure 3A:
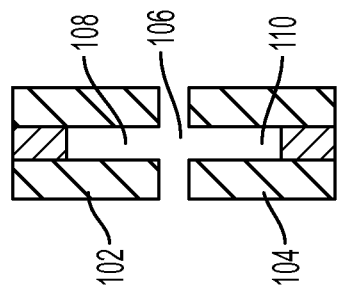
FIG. 3A is a cross-sectional view of the ring of FIG. 2, taken along plane A-A as indicated in FIG. 2, showing a track formed within the ring.
Figure 3B:
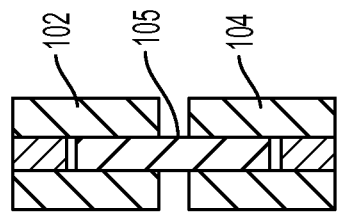
FIG. 3B is a cross-sectional view of the ring of FIG. 2, taken along plane B-B as indicated in FIG. 2, showing a clip positioned in the track.

FIGS. 2, 3A, and 3B show an exemplary annular prosthetic device, or ring, 100 comprising an inner frame 102, an outer frame 104, and a plurality of suture clips 105 spaced apart around the ring 100 between the inner and outer frames. The inner frame 102 and the outer frame 104 can each have a generally U-shaped cross-section with opposing cavities or tracks 108, 110, respectively (FIGS. 3A-3B). The opposing cavities 108, 110 and the open region between the cavities can form a continuous or semi-continuous track 106 extending around the ring 100. The inner and outer frames 102, 104 can be unconnected to each other except for the suture clips in some embodiments, while in other embodiments the ring 100 can include support struts (not shown) extending between the inner and outer frames to keep their desired spacing relative to each other.

The suture clips 105 are positioned within a continuous track 106 partially retained in the recess 108 of the inner frame 102 and partially retained in the recess 110 of the outer frame 110. In some embodiments, some or all of the suture clips 105 can slide along the track 106 around the ring 100 to different positions. One or more of the suture clips can also be fixed to the inner and/or outer frames.

Some or all of the suture clips 105 can be configured to rotate (i.e., spin) and/or translate (i.e., slide) within the track 106. The sliding movement can comprise longitudinal movement at least partially along the annular path of the ring 100. However, depending upon the width of the track 106, the clips 105 can also be configured to move slightly in a direction perpendicular to the annular path of the ring 100. In some cases, one or more of the clips 105 are fixed to the inner frame 102 and/or the outer frame 104 (such as by welding or an adhesive), while the other suture clips are floating in the track 106 (i.e., can slide and spin).

For example, in one embodiment, the ring 100 can comprise three fixed suture clips spaced around the ring to maintain the desired spaced relationship between the inner and outer frames 102, 104, while the other suture clips are free to spin and slide along the track 106 between the fixed clips. In some embodiments, one or more of the clips can spin in place within the recess, but cannot slide along the track 106. Having one or more clips that cannot slide along the track can prevent all of the clips from bunching together on one side of the ring 100, which could undesirably allow the outer frame 104 to separate from the inner frame 102 and release the clips.

The surgeon or other user can thus adjust the longitudinal position and/or rotational orientation of one or more of the clips 105 within the ring 100 at any time, such as before introducing the ring 100 into the patient's body or after passing the ring 100 over an array of sutures and parachuting the ring down to the native valve annulus region.

In some embodiments, the surgeon or other user can make one or more adjustments to move the clips 105 to a desired orientation within the ring 100 and then fix the clips in position relative to the frames 102, 104 such that the clips can no longer move relative to the frames. This can be accomplished, for example, by clamping the frames securely onto the edges of the clips, or applying an adhesive, or by welding the clips to the frames.

In some embodiments, the ring 100 can comprise one or more non-clip supports (not shown) that extend between the inner frame 102 and the outer frame 104. Such supports can connect the opposing upper lips of the two frames, or can connect the opposing lower lips of the two frames, for example. In some embodiments, these non-clip supports may not inhibit movement of the clips 105 along the track 106. For example, the clips may be free to slide under or over the non-clip supports that bridge the inner and outer frames together. Any number of such non-clip supports can be included, and in any positions around the ring 100.

In some embodiments, the ring 100 can comprises one or more internal walls or other physical barriers within the track 106 to prevent the clips 105 from sliding outside of a desired segment of the ring 100. These walls or barriers can also provide structural support for the ring 100, such as to keep the desired spacing between the upper and lower lips of the frame.

The ring 100 can comprise open spaces between adjacent clips 105 and between the inner and outer frames 102, 104. These open spaces can allow for the placement of additional sutures and/or other objects through the ring, and can allow for tissue ingrowth through the open regions when implanted.

In some embodiments, the suture clips 105 can be partially opened prior to suture placement through the clips by positioning a temporary object through the suture clips. For example, each suture clip can have a flat wire extending between the two tabs of the suture clip such that the flat wire partially separates the two tabs and facilitates inserting a suture through between the tabs. After placement of the sutures, the flat wires or other objects can be removed to allow the two tabs of each clip to clamp down on the sutures.

FIGS. 4A-4C provide detailed views of some exemplary suture clip configurations that can be incorporated with the ring 100. FIG. 4A shows a suture clip 200 that comprises a generally disk-shaped body (which can be circular) having an annular outer edge 212 and two tabs 214, 216 that extend inwardly from the outer edge. Each tab 214, 216 is shaped generally in a half-circle or semi-lunar shape. The tabs 214, 216 are separated from the outer body 212 at their sides by curved slots 218, 220 and are separated from each other by a straight slit 222 generally bifurcating the clip. The curved slots 218, 220 and middle slit 222 connect to each other but do not intersect with an outer edge 212, thus forming a "closed" generally H-shaped opening extending through the clip from one face of the clip to the other.

As shown in FIG. 4B, one or more sutures 208 can be inserted into the slit 222 from either the top or the bottom, deflecting both tabs 214, 216 in the direction of insertion.

Once the sutures 208 are inserted as shown in FIG. 4B, the clip 200 becomes biased and allows the sutures to move axially upward with little resistance but prevents the sutures from moving axially downward. In some embodiments, the gripping edges of the tabs 214, 216 can be sharp, which can provide better grip on the sutures, and in other embodiments the gripping edges of the tabs can be rounded, which can reduce the likelihood of damaging and/or cutting the sutures. In some implementations of the clip 200, the two tabs 214, 216 can be elastically deformed in opposite directions with one tab bending upwardly out-of-plane and the other tab bending downwardly out-of-plane. This can lock the sutures from sliding in either direction through the clip 200. In some embodiment, the clip 200 can grip the suture 208 tighter when tension is increased on an engaged end of the suture, creating a self-tightening locking mechanism that prevents the ring 100 from loosening from the tissue after the sutures have been pulled tight. This can obviate the need for tying knots in each of the sutures above the ring 100, which reduces the time of the procedure. Furthermore, if a sutures are too loose after an initial tightening, free ends of the suture can be pulled tighter relative to the ring to reduce the slack in the engaged end of the sutures.

FIG. 4C shows an alternative suture clip 300 wherein the tabs 314, 316 include jagged gripping regions 324, such as one per suture segment that is to be engaged by the clip, to help contain the sutures within the slit 322 and prevent lateral sliding of the sutures into the curved slots 318, 320. Within each jagged region 324, one or both of the tabs 314, 316 can comprise one or more protruding portions that are received by one or more complementary receiving portions in the other tab. In some embodiments, the clip 300 can comprise one continuous jagged region for gripping two or more suture segments. In other embodiments, the clip 300 can comprise three or more jagged regions. The suture clip 300, or any of the suture clips disclosed herein, can also include recesses 330 on its lateral sides behind each tab 314, 316 to provide a gripping location for a clamping tool. Such a clamping tool can pinch the suture clip 300 to cause the tabs 314, 316 deflect out of plane and open the slit 322 to allow insertion of sutures.

A wide variety of suture clip designs and configurations can be used in the prosthetic devices disclosed herein, many examples of which are described herein. Additional suitable suture clip configurations are disclosed in U.S. Patent Pub. No. 2014/0031864, published Jan. 30, 2014, and entitled "Suture Securement Devices," which is incorporated by reference herein in its entirety. In some embodiments, the prosthetic devices disclosed herein can comprise more than one type of suture clip.

In some embodiments, one or more of the suture clips 105 can be removed from the ring 100 and/or one more additional suture clips can be inserted into the track 106 of the ring 100. This may be accomplished be temporarily deforming the inner or outer frames to allow access to the track 106.

For purposes of this description, certain aspects, advantages, and novel features of the embodiments of this disclosure are described herein. The disclosed methods, devices, and systems should not be construed as limiting in any way. Instead, the present disclosure is directed toward all novel and nonobvious features and aspects of the various disclosed embodiments, alone and in various combinations and subcombinations with one another. The methods, devices, and systems are not limited to any specific aspect or feature or combination thereof, nor do the disclosed embodiments require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the term "and/or" used in a list of elements means any one or more of the listed elements. For example, the phrase "A, B, and/or C" means "A," "B," "C," "A and B," "A and C," "B and C" or "A, B and C."

As used herein, the term "coupled" generally means physically or electrically linked and does not exclude the presence of intermediate elements between the coupled items absent specific contrary language.

In view of the many possible embodiments to which the principles of the disclosed technology may be applied, it should be recognized that the illustrated embodiments are only preferred examples and should not be taken as limiting the scope of the disclosure. Rather, the scope of the disclosure is at least as broad as the following claims. I therefore claim all that comes within the scope of these claims.

The invention claimed is:

1. An annular device for implantation at a native heart valve annulus, comprising:
  an annular frame having an open central region; and
  a plurality of suture clips spaced angularly apart around the annular frame, wherein the plurality of suture clips are integral with the annular frame, permanently fixed to the annular frame, or contained within the annular frame;
  wherein each of the suture clips comprises two substantially equal sized opposing tabs that extend toward each other such that the suture clip forms a gripping region between ends of the tabs, the gripping region configured to grip a suture inserted through the suture clip between the two tabs; and
  wherein the suture clips are configured to engage sutures inserted through the gripping region to restrict the inserted sutures from moving through the suture clips in a direction opposite of insertion.

2. The device of claim 1, wherein the annular frame and the plurality of suture clips are integral with one another and formed from a single piece of material.

3. The device of claim 1, wherein the annular frame is generally D-shaped and configured for placement at a native mitral valve annulus.

4. The device of claim 1, wherein the gripping region comprises at least one jagged gripping region configured restrict an inserted suture from moving laterally out of the gripping region.

5. The device of claim 4, wherein the gripping region comprises two jagged regions each configured to receive a suture.

6. The device of claim 1, wherein the annular frame comprises an annular outer frame portion and an annular inner frame portion that is spaced radially inwardly from the outer frame portion, and wherein the inner frame portion and the outer frame portion define an intermediate region between the inner and outer frame portions within which the plurality of suture clips are positioned.

7. The device of claim 6, wherein the intermediate region also includes a plurality of apertures or open regions positioned between the suture clips.

8. The device of claim 1, wherein the suture clips comprise two opposing slits on opposite sides of the tabs, and the gripping region connects the two opposing slits.

9. The device of claim 8, wherein the two opposing slits are arcuate.

10. The device of claim 1, wherein the device is configured to be attached to a prosthetic heart valve such that the device is operable to anchor the prosthetic heart valve to the native mitral valve annulus via a plurality of sutures engaged within the suture clips.

11. An annular device for implantation at a native valve annulus, comprising:
  an annular frame comprising an inner frame portion having a first cavity that faces radially outwardly, and an outer frame portion positioned radially around the inner frame portion and having a second cavity that faces radially inwardly toward the first opening, such that the first and second cavities form an annular track around the annular frame between the inner frame portion and the outer frame portion; and
  a plurality of suture clips positioned within the annular track, wherein one or more of the plurality of suture clips can slidably move along the annular track relative to the annular frame.

12. The device of claim 11, wherein each suture clip comprises an opening for insertion of at least one suture through the suture clip, and wherein an inserted suture can be advanced in only one longitudinal direction through the opening of the suture clip.

13. The device of claim 11, wherein one or more of the plurality of suture clips can rotate within the annular track relative to the frame.

14. The device of claim 13, wherein one or more of the plurality of suture clips can rotate 360° within the annular track relative to the frame.

15. The device of claim 11, wherein one or more of the plurality of suture clips cannot slidably move within the annular track relative to the frame.

16. The device of claim 11, wherein one or more of the plurality of suture clips comprises an annular outer edge, two tabs that extend inwardly from the outer edge, and at least one jagged gripping region between the two tabs.

* * * * *